United States Patent

Waldroup et al.

(10) Patent No.: US 6,740,792 B2
(45) Date of Patent: May 25, 2004

(54) COVER MATERIAL WITH IMPROVED FLUID HANDLING PROPERTIES

(75) Inventors: Donald E. Waldroup, Roswell, GA (US); Jaime Braverman, Atlanta, GA (US); Teresa Petryk, Woodstock, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 259 days.

(21) Appl. No.: 10/025,839

(22) Filed: Dec. 18, 2001

(65) Prior Publication Data

US 2003/0124927 A1 Jul. 3, 2003

(51) Int. Cl.$^7$ ................................. A61F 13/15
(52) U.S. Cl. ................ 604/365; 604/367; 604/384; 604/378; 604/370; 428/212; 442/334
(58) Field of Search .................... 604/365, 367, 604/370, 372, 378, 379, 380, 383, 384; 428/212, 213, 219; 442/334, 340, 344, 346, 361–364, 392

(56) References Cited

U.S. PATENT DOCUMENTS

| | | |
|---|---|---|
| 3,338,992 A | 8/1967 | Kinney |
| 3,341,394 A | 9/1967 | Kinney |
| 3,502,538 A | 3/1970 | Petersen |
| 3,502,763 A | 3/1970 | Hartmann |
| 3,542,615 A | 11/1970 | Dobo et al. |
| 3,692,618 A | 9/1972 | Dorschner et al. |
| 3,802,817 A | 4/1974 | Matsuki et al. |
| 3,849,241 A | 11/1974 | Butin et al. |
| 4,041,203 A | 8/1977 | Brock et al. |
| 4,118,531 A | 10/1978 | Hauser |
| 4,340,563 A | 7/1982 | Appel et al. |
| 4,636,209 A | 1/1987 | Lassen |
| 4,652,484 A * | 3/1987 | Shiba et al. ................ 442/353 |
| 4,761,322 A | 8/1988 | Raley |
| 4,762,520 A | 8/1988 | Wallström |
| 4,778,460 A | 10/1988 | Braun et al. |
| 4,795,668 A | 1/1989 | Krueger et al. |
| 4,892,534 A | 1/1990 | Datta et al. |
| 5,037,409 A | 8/1991 | Chen et al. |
| 5,108,820 A | 4/1992 | Kaneko et al. |
| 5,364,382 A | 11/1994 | Latimer et al. |
| 5,382,400 A | 1/1995 | Pike et al. |
| 5,429,629 A | 7/1995 | Latimer et al. |
| 5,437,653 A | 8/1995 | Gilman et al. |
| 5,456,971 A | 10/1995 | Fahmy |
| 5,466,513 A | 11/1995 | Wanek et al. |
| 5,679,042 A | 10/1997 | Varona |
| 5,705,249 A | 1/1998 | Takai et al. |
| 5,853,628 A * | 12/1998 | Varona ........................ 264/6 |
| 5,965,468 A | 10/1999 | Marmon et al. |
| 5,968,025 A | 10/1999 | Roe et al. |
| 6,001,751 A * | 12/1999 | Pereira et al. ............. 442/334 |
| 6,362,391 B1 * | 3/2002 | Mizutani et al. ........... 604/379 |
| 6,613,704 B1 * | 9/2003 | Arnold et al. ............. 442/361 |

FOREIGN PATENT DOCUMENTS

| | | |
|---|---|---|
| DE | 90 03 998.8 | 4/1991 |
| EP | 792 629 | 9/1997 |

* cited by examiner

*Primary Examiner*—Weilun Lo
*Assistant Examiner*—Jacqueline F Stephens
(74) *Attorney, Agent, or Firm*—Pauley Petersen & Ericson

(57) ABSTRACT

A material having a multi-denier base material layer including a plurality of fine denier fibers, the fine denier fibers of less than about 10 dpf, and a plurality of large denier filaments intermixed with the fine denier fibers which form channels in a longitudinal direction of the material, the large denier filaments of greater than about 10 dpf. A method of producing a multi-denier cover material is also disclosed.

53 Claims, 2 Drawing Sheets

COVER MATERIAL WITH IMPROVED FLUID HANDLING PROPERTIES

FIELD OF THE INVENTION

This invention is directed to a fabric or material suitable for use as a cover material or bodyside liner for a personal care absorbent article having improved fluid handling properties.

BACKGROUND OF THE INVENTION

Almost all personal care absorbent articles include a cover material or a bodyside liner, an absorbent structure or core underlying the cover material, and some type of backing material which is generally liquid impervious to help prevent leakage. The types of cover materials generally fall into two main groups based, at least in part, upon performance and aesthetic preferences. For example, in the area of feminine care and sanitary napkins, the market is polarized into two segments, women who prefer clean and dry film covers and women who prefer soft, cloth-like nonwoven covers. The advantage of film covers for sanitary napkins is that they provide a relatively clean and dry surface as menses tends to pass through the film layer and into the interior of the absorbent product. A drawback, however, is that such film layers do not provide the degree of softness and comfort that a nonwoven cover material can provide. An additional drawback is the smooth, slick, non-clothlike feel that is characteristic of many films. Nonwoven-based cover materials, on the other hand, are very soft and cloth-like in feel, but tend to retain more of the menses at or just below the surface of the cover material which, in turn, makes the product suffer from the standpoint of properties such as cleanliness and dryness. The difference in functionality is a direct result of the structure of nonwovens including small average pore size and nonuniform pore size distribution.

Conventional hydrophilic cover materials or bodyside liners in contact with the skin effectively transport body fluids into the absorbent core, but they cause a wet feel against the skin of the user and may adversely affect skin health. In addition, they may wick liquid in the plane of the layer, allowing liquid to approach the edges of the absorbent article and possibly leak or seep out.

To achieve the goal of softness and a dry feel in topsheets of absorbent articles, many manufacturers have turned to nonwoven fabrics made of hydrophobic fibers for the body-contacting topsheet. While the use of hydrophobic nonwoven fabrics results in improved dry feel, the hydrophobic material hinders wicking into the absorbent core causing fluid to pool on the surface until enough pressure is applied to permeate the structure under conditions of low pressure and flow. As a result, the fluid may run off the pad and leak.

To improve the poor wicking and absorbent properties of hydrophobic materials, it is known to apply a finish comprising surfactants on the surface of the hydrophobic fibers, rendering them wettable or introducing fibers which are intrinsically wettable. Intrinsically wettable fibers may be natural, such as cellulose, or synthetic, such as rayon, polyester, or polyamides. Although providing good intake properties, wettable fibers introduce higher fluid retention and more fluid staining.

In the case of absorbent pads for feminine care, two distinct approaches involving topsheets or covers are commonly employed. One approach is to use a soft, clothlike nonwoven hydrophilic material which increases comfort but has the drawback of fluid retention and staining. A second approach is to use an apertured plastic film of hydrophobic polymer or other materials. The hydrophobic cover material repels many body fluids while the apertures allow wicking away from the cover into the absorbent material below.

Accordingly, there is a need for an improved cover material which can provide the clean and dry feel characteristic of hydrophobic film cover materials while also delivering the softness of nonwoven cover materials.

SUMMARY OF THE INVENTION

The present invention is directed to a fabric or material suitable for use as a cover material or bodyside liner for a personal care absorbent article. The material exhibits a unique topography and texture that enhances the material's visual and tactile properties and also increases its permeability. When used as a cover material or bodyside liner in a personal care absorbent article, the material has superior fluid handling characteristics. Further, the dryness of the cover material is improved due to the reduced surface area of the cover material which contacts the wearer's skin.

The cover material includes a fine denier component having fibers from about 3 dpf to about 5 dpf and a large denier component having fibers or filaments from about 10 dpf to about 100 dpf. The cover material can include multiple discrete or distinct layers or the large denier filaments can be intermixed with the fine denier fibers to produce a single layer multi-denier cover material. The fine denier fibers and the large denier filaments can include the same base material, for example a polypropylene polymer material, or each can include a different base material, such as a polymer blend, to improve the softness and offset the stiffness of the large denier component.

In one embodiment of this invention, the single layer multi-denier cover material can be produced using a spunbond process, wherein the large denier filaments are spun and intermixed with the fine denier fibers. The fine denier fibers and the large denier filaments can be spun from the same spinning plates having an appropriate hole arrangement or the fibers and filaments can be spun from separate spinning plates. The filaments can be bonded to the fibers using suitable bonding methods, such as thermal bonding, through-air bonding, ultrasonic bonding and other suitable bonding methods known to those having ordinary skill in the art.

Alternatively, the cover material having distinct layers of fine denier fibers and the large denier filaments can be produced. A base material layer, for example a 0.5 osy spunbond nonwoven web having fine denier fibers of about 3 dpf to about 5 dpf fibers is formed. Subsequently, a plurality of streams each including a plurality or group of large denier filaments of about 10 dpf to about 100 dpf can be disposed or placed onto a surface of the base material layer. Desirably, but not necessarily, the streams of the large denier filaments are laid in a generally machine or longitudinal direction to produce a plurality of channels. The channels direct fluid to flow in a longitudinal direction rather than a lateral or cross-machine direction to reduce fluid leakage.

The separation or spacing between the streams of the high denier filaments can be controlled to tailor a cover material for specific needs. For example, in an absorbent system having relatively quick absorption, it may be desirable to have a small level of separation between the streams of the large denier filaments. Conversely, in an absorbent system having relatively slow absorption, it may be desirable to have a greater level of separation between the streams of the large denier filaments to increase the void volume in the cover material so a relatively large amount of fluid can be retained until the fluid is absorbed by the underlying absorbent structure without leakage.

With the foregoing in mind, it is a feature and advantage of the invention to provide a material suitable for use as a cover material or bodyside liner for a personal care absorbent article having improved fluid handling characteristics.

It is further a feature and advantage of the invention to provide a cover material or bodyside liner for a personal care absorbent article having a unique topography and texture as well as enhanced visual and tactile properties.

It is further a feature and advantage of the invention to provide a method for producing a material having a fine denier component including fine denier fibers of about 3 dpf to about 5 dpf and a large denier component including large denier fibers of about 10 dpf to about 100 dpf.

DEFINITIONS

Within the context of this specification, each term or phrase below will include the following meaning or meanings.

"Disposable" refers to garments or articles which are designed to be discarded after a limited use rather than being laundered or otherwise restored for reuse.

"Disposed," "disposed on," and variations thereof are intended to mean that one element can be integral with another element, or that one element can be a separate structure bonded to or placed with or placed near another element.

"Elastic," "elasticized" and "elasticity" mean that property of a material or composite by virtue of which it tends to recover its original size and shape after removal of a force causing a deformation.

"Elastomeric" refers to a material or composite which can be elongated by at least 50 percent of its relaxed length and which will recover, upon release of the applied force, at least 40 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Fabrics" is used to refer to all of the woven, knitted and nonwoven fibrous webs.

"Film" refers to a thermoplastic film made using a film extrusion and/or foaming process, such as a cast film or blown film extrusion process. The term includes apertured films, slit films, and other porous films which constitute liquid transfer films, as well as films which do not transfer liquid.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "non-wettable" or hydrophobic.

"Layer" when used in the singular can have the dual meaning of a single element or a plurality of elements.

"Liquid impermeable" when used to describe a layer or laminate means that liquid, such as urine or menses, will not pass through the layer or laminate under ordinary use conditions in a direction generally perpendicular to the plane of the layer or laminate at the point of liquid contact.

"Liquid permeable" refers to a layer or laminate that is not liquid impermeable.

Figure 1:
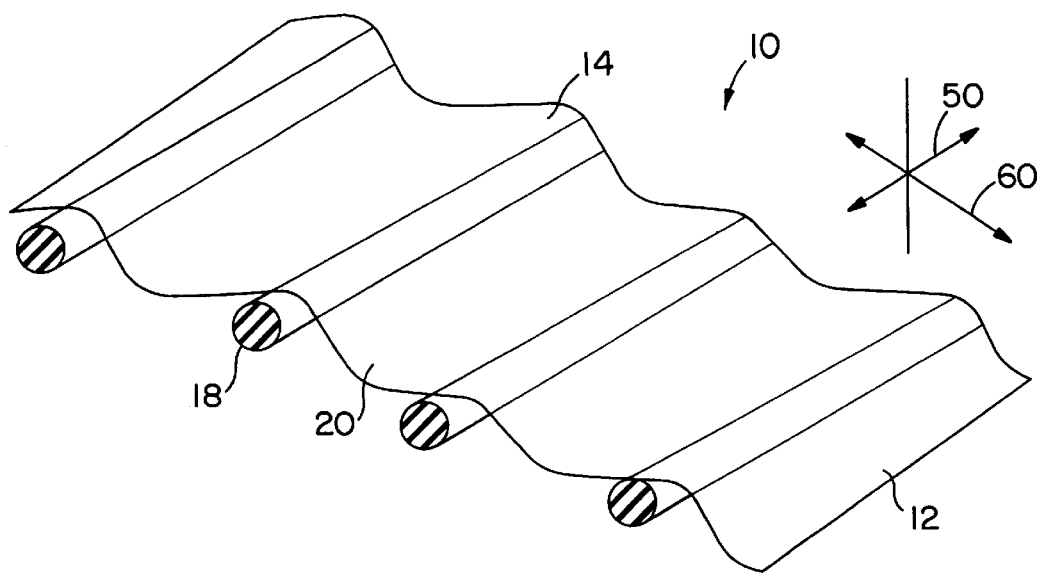
FIG. 1 is schematic perspective view of a material suitable for a cover material or bodyside liner for a personal care absorbent article, according to one embodiment of this invention.

"Longitudinal" and "transverse" have their customary meaning, as indicated by the longitudinal and transverse axes depicted in FIG. 1. The longitudinal axis lies in the plane of the material. The transverse axis lies in the plane of the material generally perpendicular to the longitudinal axis.

"Meltblown fiber" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter which may create microfibers. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 0.6 denier, and are generally self bonding when deposited onto a collecting surface. Meltblown fibers used in the present invention are preferably substantially continuous in length.

"Nonwoven" and "nonwoven fabric or web" refer to materials and webs of material which are formed without the aid of a textile weaving or knitting process.

The "nonwoven web" materials have a structure of individual fibers or threads which are interlaid, but not in an identifiable, repeating manner. Nonwoven fabrics or webs have been, in the past, formed by a variety of processes such as, for example, meltblowing processes, spunbonding processes and bonded carded web processes. The basis weight of nonwoven fabrics is usually expressed in ounces of material per square yard (osy) or grams per square meter (gsm) and the fiber diameters are usually expressed in microns. Note that to convert from osy to gsm, multiply osy by 33.91.

"Personal care product" means products for the absorption of body exudates, such as diapers, training pants, disposable swim wear, absorbent underpants, adult incontinence products, bandages, veterinary and mortuary products, and feminine hygiene products like sanitary napkins and pantiliners.

"Polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

"Spunbond fiber" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average deniers larger than about 0.3, more particularly, between about 0.6 and 10.

"Surface" includes any layer, film, woven, nonwoven, laminate, composite, or the like, whether pervious or impervious to air, gas, and/or liquids.

"Thermoplastic" describes a material that softens when exposed to heat and which substantially returns to a non-softened condition when cooled to room temperature.

These terms may be defined with additional language in the remaining portions of the specification.

DETAILED DESCRIPTION OF THE INVENTION

The present invention is directed to a fabric or material suitable for use as a cover material or bodyside liner for a personal care absorbent article. The material comprises a fine denier component including fine denier fibers less than about 10 dpf, desirably about 2 dpf to abut 8 dpf, more desirably about 3 dpf (denier per fiber) to about 5 dpf and a large denier component having large denier fibers or filaments desirably greater than about 10 dpf, more desirably greater than about 15 dpf. For example, desirably about 10 dpf to about 100 dpf, more desirably about 15 dpf to about 40 dpf. The resulting material exhibits a unique texture that enhances the visual and tactile properties and also exhibits high permeability. The material has a topography which provides a channeling effect whereby fluids are removed to a desired location in an absorbent structure. Thus, the material is suitable as a cover material or a bodyside liner for a personal care absorbent article, having improved fluid handling properties.

The principles of the present invention can be incorporated into any suitable personal care absorbent article. Examples of such suitable articles include diapers, training pants, feminine hygiene products, incontinence products, other personal care and health care garments, and the like. For ease of explanation, the description hereafter will be in terms of a cover material or bodyside liner for use in a suitable personal care absorbent article. It is apparent to those having ordinary skill in the art the material of the present invention may be included in any suitable component in a personal care absorbent article.

The cover material is desirably compliant, soft feeling, non-irritating to the wearer's skin and liquid permeable. The cover material can be less hydrophilic than an absorbent structure positioned underneath the cover material to present a relatively dry surface to the wearer and permit liquid to readily penetrate through its thickness.

The cover material may include a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the cover material. For example, the cover material can be composed of a meltblown or spunbond web of polyolefin fibers. The cover material can also be a bonded-carded web composed of natural and/or synthetic fibers. The cover material can be composed of a substantially hydrophobic material, and the hydrophobic material can, optionally, be treated with a surfactant or otherwise processed to impart a desired level of wettability and hydrophilicity. For example, the material can be surface treated with about 0.28 weight percent of a surfactant commercially available from the Rohm and Haas Co. under the trade designation Triton X-102. Other suitable surfactants are commercially available from Uniqema Inc., a division of ICI of New Castle, Del., under the trade designation Ahcovel, and from Cognis Corporation of Ambler, Pa., produced in Cincinnati, Ohio, and sold under the trade designation Glucopon 220. The surfactant can be applied by any conventional means, such as spraying, printing, brush coating or the like. The surfactant can include botanic extract or any suitable component that can help in the skin wellness of the user. The surfactant can be applied to the entire cover material or can be selectively applied to particular sections of the cover material, such as the medial section along the longitudinal centerline.

The cover material may include a suitable liquid permeable nonwoven bicomponent web. The nonwoven bicomponent web can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. Further, the cover material can include elastic, elastomeric or extensible materials.

In accordance with one embodiment of this invention, the cover material 10 comprises a base material layer 12 including a fine fiber component. The base material layer 12 may be any type of thermoplastic nonwoven web or apertured film. For instance, the base material layer 12 may be a spunbond web, a meltblown web, a bonded carded web, or a combination including any of the above. Desirably, the base material layer 12 is a spunbond web. For example, the base material layer 12 may comprise a 0.5 osy or a 0.7 osy spunbond web having a plurality of fine denier fibers 14.

A wide variety of thermoplastic polymer materials can be used to make the base material layer 12. Exemplary polymer materials include without limitation, polypropylene, polyethylene (high and low density), ethylene copolymers with $C_3$–$C_{20}$ α-olefins, propylene copolymers with ethylene or $C_4$–$C_{20}$ α-olefins, butene copolymers with ethylene, propylene, or $C_5$–$C_{20}$ α-olefins, polyvinyl chloride, polyesters, polyamides, polyfluorocarbons, polyurethane, polystyrene, polyvinyl alcohol, caprolactams, and cellulosic and acrylic resins. Bicomponent and biconstituent thermoplastic webs may also be utilized, as well as webs containing blends of one or more of the above-listed thermoplastic polymers. The base material layer 12 desirably has a basis weight of about 0.4 ounces per square yard (osy) to about 1.0 osy, more desirably about 0.5 osy to about 0.7 osy and desirably have a thickness of about 0.008 inch to about 0.08 inch, more desirably about 0.011 inch to about 0.04 inch.

Desirably, the fine denier fibers 14 are less than about 10 denier per fiber (dpf), more desirably about 2 dpf to about 8 dpf, still more desirably about 3 dpf to about 5 dpf. The fine denier fibers 14 are desirable for surge functionality since the fine denier fibers yield a material having a small pore structure resulting in higher capillary tension and improved fluid management. Small denier fibers also provide a softer feel that improves the user comfort. The cover material 10 may include more than one base material layer 12. The subsequent layers can have a different denier, permeability, and/or wettability to promote fluid absorption in which a gradient is created promoting the fluid transport through the layer. Additionally, a second and subsequent layers can be apertured individually or coapertured with the first layer to improve the material absorption behavior.

In accordance with one embodiment of the invention, the base material layer 12 may include a plurality of large denier fibers or filaments 18. During the spunbond process discussed below, the large denier filaments 18 can be intermixed with the fine denier fibers 14. The large denier filaments 18 can comprise the same polymer or polymer blend as the fine denier fibers 14 or a different polymer or polymer blend. Suitable thermoplastic polymer materials for making the large denier filaments 18 include those thermoplastic polymer materials used to make the fine denier fibers 14, discussed above. In one embodiment of this invention, the large denier filaments 18 comprise bicomponent filaments. Suitable bicomponent staple filaments include a polyethylene/polypropylene bicomponent fiber available from CHISSO Corporation, Osaka, Japan. In this particular bicomponent filament, the polypropylene forms the core and the polyethylene forms the sheath of the filament. Other filament orientations are possible, such as multi-lobe, side-by-side, end-to-end, or the like.

In one embodiment of this invention, the large denier filaments 18 can include elastic, elastomeric or extensible materials. Suitable polymer or polymer blends used to prepare the elastic large denier filaments 18 herein include olefin polymers, such as an olefinic copolymer of polyethylene. More specifically, other suitable polymers include diblock, triblock, tetrablock or other multi-block elastomeric copolymers such as olefinic copolymers, including styrene-isoprene-styrene, styrene-butadiene-styrene, styrene-ethylene/butylene-styrene, or styrene-ethylene/propylene-styrene, which may be obtained from Kraton Inc., under the trade designation KRATON® elastomeric resin; polyurethanes, including those available from E. I. Du Pont de Nemours Co., under the trade name LYCRA® polyurethane; polyamides, including polyether block amides available from Ato Chemical Company, under the trade name PEBAX® polyether block amide; polyesters, such as those available from E. I. Du Pont de Nemours Co., under the trade name HYTREL® polyester; and single-site or metallocene-catalyzed polyolefins having a density less than about 0.89 grams/cc, available from Dow Chemical Co. under the trade name AFFINITY®.

The large denier filaments 18 desirably are greater than about 10 dpf, more desirably about 10 dpf to about 100 dpf, still more desirably about 15 dpf to about 40 dpf. The large denier filaments 18 can have a uniform size distribution or can have a variable size distribution. Further, the large denier filaments 18 can be colored or a pigment or pigments can be added for enhanced appearance. The large denier filaments 18 can be placed in a generally parallel alignment or in a generally random alignment.

Alternatively, groups or streams of the large denier filaments 18 may be disposed or placed on the base material layer 12 comprising the fine denier fibers 14 desirably in a generally machine or longitudinal direction 50 to produce a plurality of channels 20 between adjacent streams of the large denier filaments 18. The channels 20 direct fluid to flow in the longitudinal direction 50 rather than a lateral or cross-machine direction 60. Further, the streams of the large denier filaments 18 produce the channels 20 having a depth such that a surface area of the cover material 10 contacting the skin of a wearer is reduced. The cover material 10 in the area of the streams of the large denier filaments 18 contact the wearer's skin while the surface area of the cover material 10 between the adjacent streams of the large denier filaments 18 does not contact the wearer's skin. The separation of the cover material 10 from the wearer's skin provides a dry cover material 10.

Figure 2:
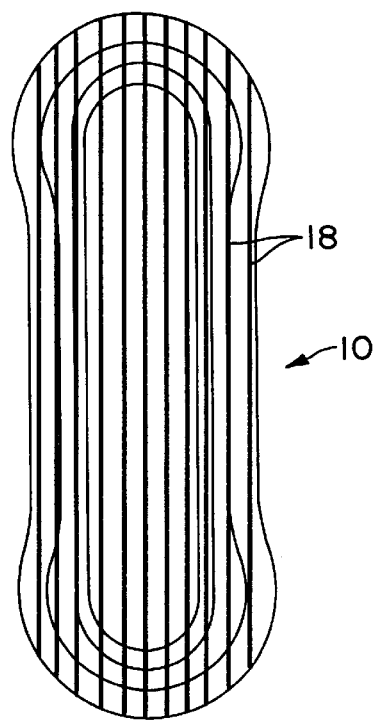
FIG. 2 is a schematic top view of a feminine care product having a cover material including large denier filaments aligned in a generally parallel orientation, according to one embodiment of this invention.
Figure 3:
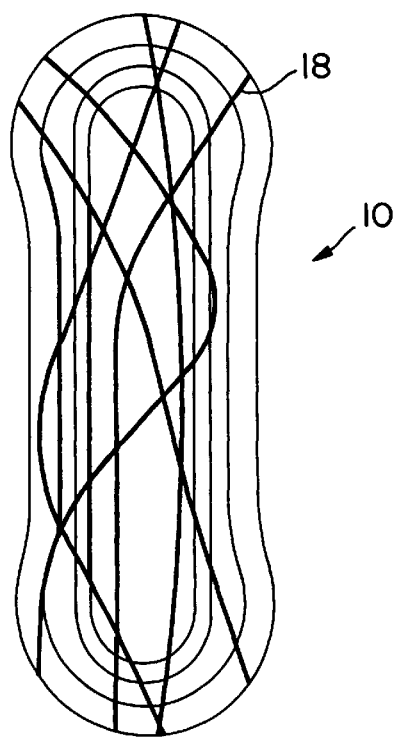
FIG. 3 is a schematic top view of a feminine care product having a cover material including generally randomly aligned large denier filaments, having a machine direction (MD) orientation, according to one embodiment of this invention.

In one embodiment of this invention, the large denier filaments 18 can be placed in a generally parallel alignment. For example, as shown in FIG. 2, a feminine care product having the cover material 10 in accordance with one embodiment of this invention can include large denier filaments 18 aligned in a generally parallel orientation. Alternatively or in addition, at least a portion of the large denier filaments 18 can be placed in a random alignment. For example, as shown in FIG. 3, a feminine care product having the cover material 10 in accordance with this invention can include generally randomly aligned large denier filaments 18, desirably having a machine direction (MD) orientation.

Adjacent streams of the large denier filaments 18 can be spaced apart or separated by a predetermined distance to produce a cover material 10 for specific needs. For example, in an absorbent system having relatively quick absorption, it may be desirable to have a small level of separation between the large denier filaments 18. Conversely, in an absorbent system having relatively slow absorption, it may be desirable to have a greater level of separation between the large denier filaments 18 to increase the void volume in the cover material 10 so a large amount of fluid can be retained until the fluid is absorbed by the underlying absorbent structure. Alternatively, the distance between the streams of the large denier filaments 18 may vary across a width of the cover material 10 to provide areas of the cover material 10 having relatively greater or lesser degree of absorption. Desirably, the streams of the large denier filaments 18 are spaced apart along the width of the cover material by about 1.0 mm to about 15 mm, more desirably about 3 mm to about 8 mm.

Whether combined with the fine denier fibers 14 to produce a single layer multi-denier cover material 10 or disposed on the base material layer 12 to form a cover material 10 having distinct layers, the large denier filaments 18 are bonded to the fine denier fibers 14 using any suitable bonding means, such as thermal bonding, adhesive bonding, ultrasonic bonding and any other suitable means known to those having ordinary skill in the art. Desirably, the large denier filaments 18 are thermally bonded to the fine denier fibers 14 using suitable thermal bonding means, such as standard heat rolls, ultrasound and through-air-bonding.

In one embodiment of the invention, a second layer of material can be placed below or on the large denier filaments 18 to secure the large denier filaments 18 with respect to the fine denier fibers 14. The second layer can have a different permeability, pore structure and/or wettability than the base material layer 12 to further promote fluid absorption. This layer can be apertured or coapertured with the base material layer 12 to improve the permeability.

In accordance with one embodiment of this invention, the cover material 10 is produced using a spunbond process. The fibers 14 and filaments 18 each can include the same polymer or polymer blend or different polymer or polymer blend. For example, the fine denier fibers 14 and the large denier filaments 18 each can include a polypropylene polymer material. In one embodiment wherein the fine denier fibers 14 are intermixed with the large denier filaments 18 in a multi-denier cover material 10, the fibers 14 and the filaments 18 can be spun from the same spinning plate having an appropriate spinning hole arrangement. Alternatively, the fibers 14 and the filaments 18 can be spun from separate spinning plates and intermixed or combined to form the multi-denier cover material 10. The fibers 14 and the filaments 18 can then be bonded together by any suitable bonding means, such as thermal bonding, adhesive bonding, ultrasonic bonding and other means known to those having ordinary skill in the art.

Alternatively, the fine denier fibers 14 and the large denier filaments 18 can include distinct layers of the cover material 10. For example, the base material layer 12 may include a 3 dpf to about 5 dpf spunbond web produced by the spunbond process. After the spunbond web including the fine denier fibers 14 is produced, a plurality of streams including the large denier filaments 18 are placed on the surface of the spunbond web to produce channels 20. As discussed above, the streams including the large denier filaments 18 can be placed at a predetermined distance from adjacent large denier filaments 18 depending on the required absorbency or fluid handling capabilities of the cover material 10. Further, a height of the streams of the large denier filaments 18 can vary to produce channels 20 having a desired depth. The large denier filaments 18 can have any suitable cross section, such as circular, pyramidal and other suitable cross sections known to those having ordinary skill in the art. In certain embodiments of this invention, the higher denier fibers 18 can be incorporated into a prebonded nonwoven material during an off-line process or in a converting line, for example.

EXAMPLES

Exemplary cover materials including a plurality of large denier filaments forming channels and a spunbond layer of fine denier fibers were tested for intake and rewet characteristics and compared to a typical cover material for a personal care absorbent article, for example a feminine pad cover. All codes were bench tested on top of a current 250 gsm airlaid material which was on top of a 175 gsm airlaid material.

Code 1 was a control code made of a conventional cover material for a feminine pad formed of 0.6 osy spunbond material. Code 2 was a cover material made in accordance with the invention including polypropylene large denier filaments (average dpf of about 50 dpf) on a spunbond layer of fine denier fibers (average dpf of about 3.5 dpf, similar to Code 1). Code 3 was a cover material made in accordance with the invention including Kraton®-based large denier filaments (average dpf of about 50 dpf) on a spunbond layer of fine denier fibers (average dpf of about 3.5 dpf, similar to Code 1). Codes 1, 2 and 3 were tested for intake time and rewet using test methods discussed below. The test results are displayed in Table 1.

The intake time for Codes 2 and 3 were at parity with the intake time for Code 1. The results of the bench testing performed shows that the re-wet values of Codes 2 and 3 have been significantly reduced by the addition of the larger filaments when compared to the control (Code 1). Wicking was 0.25 inch longer for Codes 2 and 3, showing better fluid management in a MD or "y" direction.

TABLE 1

INTAKE TIME AND REWET

| CODE | INTAKE TIME (sec.) | REWET (grams) |
|---|---|---|
| 1 | 34.33 | 0.25 |
| 2 | 26.34 | 0.07 |
| 3 | 34.06 | 0.04 |

TABLE 2

TRIPLE GUSH TEST

| Code | 1st Insult (seconds) | 2nd Insult (seconds) | 3rd Insult (seconds) | Stain Length (cm) | Stain Width (cm) | Stain Area (cm²) |
|---|---|---|---|---|---|---|
| 1 | 92 | 540 | — | 4.73 | 1.0 | 4.73 |
| 2 | 110 | 95 | 540 | 6.05 | 0.9 | 5.44 |

Referring to TABLE 2, the systems were tested over the same absorbent materials as the example of TABLE 1. In the case of code 1, the timer was stopped after 9 minutes (540 seconds), because this time is considered too slow for an absorption system. Thus, a $3^{rd}$ insult was not performed on code 1.

Code 2 showed faster absorption as compared to Code 1. Additionally, the fluid wicked a longer distance in the product machine direction ("Y" axis). The advantage of this material is that the fluid has a preferential longitudinal absorption path that is created when the fluid wicks in the direction of the larger fibers. This reduces the probability of fluid wicking in the product cross direction that can lead to premature leakage.

Test Methods

A. Rate Block Intake Test

Figure 4:
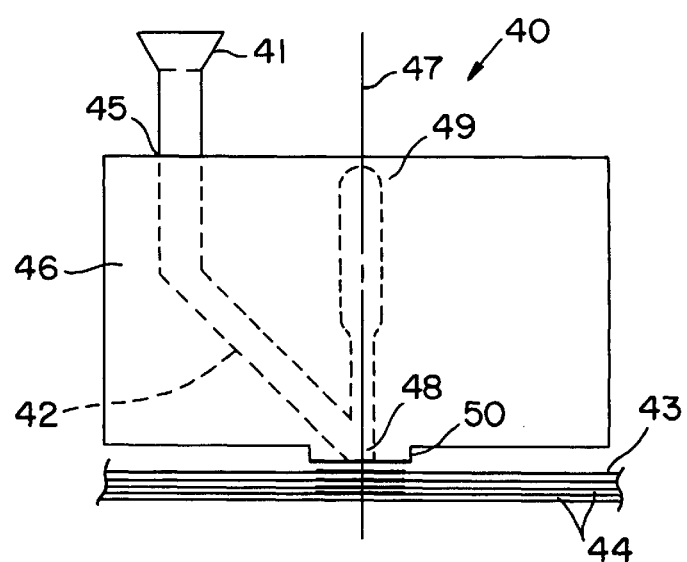
FIG. 4 is a schematic diagram of a rate block apparatus suitable for use in determining fluid intake time of a material or material systems.

This test is used to determine the intake time of a known quantity of fluid into a material and/or material system. The test apparatus consists of a clear, preferably acrylic, rate block 40, as shown in FIG. 4, and a timer or a stopwatch. A 4 inch×4 inch (102 mm by 102 mm) piece of cover material 43 to be tested is die cut. (The specific cover materials to be tested are described in the specific examples.) The absorbent material 44 used for these studies was standard and consisted of a 250 g/m² airlaid material made of 90% NF401 pulp and 10% Kosa T-255 fiber binder, 0.14 g/cc placed on top of a 175 gsm airlaid material made of 90% NF405 pulp and 10% Kosa T-255 fiber binder, 0.08 g/cc.

The rate block 40 is 3 inches (76.2 mm) wide and 2.87 inches (72.9 mm) deep (into the page) and has an overall height of 1.125 inches (28.6 mm) which includes a center area 50 on the bottom of the rate block 40 that projects farther from the main body of the rate block 40 and has a height of 0.125 inch (3.2 mm) and a width of 0.886 inch (22.5 mm). The rate block 40 has a capillary 42 with an inside diameter of 0.186 inch (4.7 mm) that extends diagonally downward from one side 46 to the center line 47 at an angle of 21.8 degrees from the horizontal. The capillary 42 may be made by drilling the appropriately sized hole from the side 46 of the rate block 40 at the proper angle beginning at a point 0.726 inch (18.4 mm) above the bottom of the rate block 40; provided, however, that the starting point of the drill hole in the side 46 must be subsequently plugged so that test fluid will not escape there. The top hole 45 has a diameter of 0.312 inch (7.9 mm), and a depth of 0.625 inch (15.9 mm) so that it intersects the capillary 42. The top hole 45 is perpendicular to the top of the rate block 40 and is center 0.28 inch (7.1 mm) from the side 46. The top hole 45 is the aperture into which the funnel 41 is placed. The center hole 48 is for the purpose of viewing the progression of the test fluid and is actually of an oval shape into the plane of FIG. 4. The center hole 48 is centered width-wise on the rate block 40 and has a bottom hole width of 0.315 inch (8 mm) and length of 1.50 inches (38.1 mm) from the center to center of 0.315 inch (8 mm) diameter semi-circles making up the ends of the oval. The oval enlarges in size above 0.44 inch (11.2 mm) from the bottom of the rate block 40, for ease of viewing, to a width of 0.395 inch (10 mm) and a length of 1.930 inches (49 mm). The top hole 49 and center hole 48 may also be made by drilling.

The sample or cover material 43 to be tested is placed over the absorbent 44 and the rate block 40 is placed on top of the materials. Two ml of an artificial menses fluid is delivered into the test apparatus funnel 41 and a timer started. The artificial menses fluid may be prepared in accordance with U.S. Pat. No. 5,883,231, the disclosure of which is incorporated herein by reference. The fluid moves from the funnel 41 into a capillary 42 where it was delivered to the material 43 or material system in the center of the center hole 48. Fluid typically spreads towards the ends of the center hole 48 oval. The timer is stopped when all the fluid was absorbed into the material 43 or material system as observed through the center hole 48 and the capillary 42 in the rate block 40. The intake time for a known quantity of test fluid is recorded for a given material or material system. This value is a measure of a material or material system's absorbency. Lower intake time represents more absorbent systems. Each type of sample is subjected to five repetitions of testing and the results are averaged to produce a single value.

B. Rewet Test

This test is used to determine the amount of fluid that will come back to the surface when a load is applied. The amount of fluid that comes back through the surface is called the "rewet" value. The more fluid that comes to the surface, the larger the "rewet" value. Lower rewet values are associated with a dryer material and hence a dryer product. In considering rewet, three properties are important: (1) intake, if the material/system does not have good intake then fluid can rewet, (2) ability of absorbent to hold fluid (the more the absorbent holds onto the fluid the less is available for rewet), and (3) flowback, the more the cover prohibits fluid from coming back through the cover, the lower the rewet. In our case, we are evaluating a cover system where the absorbent system is kept constant and, thus, we are only concerned with properties (1) and (3), intake and flowback, respectively.

A 4"×4" piece of the absorbents and the cover material was die cut. The specific cover materials are described above. After the intake test is performed, the fluid is allowed to interact with the system for 1 minute and the rate block rests on top of the materials. The material system, cover material and absorbent, are placed onto a bag filled with fluid. A piece of blotter paper is weighed and placed on top of the material system. The bag is traversed vertically until it comes into contact with an acrylic plate above it, thus pressing the whole material system against the plate blotter paper side first. The system is pressed against the acrylic plate until a total of 1 psi is applied. The pressure is held fixed for 3 minutes after which the pressure is removed and the blotter paper is weighed. The blotter paper retains any fluid that was transferred to it from the cover material/absorbent system. The difference in weight between the original blotter and the blotter after the experiment is known as the "rewet" value. Typically, 5 to 10 repetitions of this test were performed and average rewet was determined.

C. Triple Gush Test

The same rate block that is used in the Intake test described above is used in this method. Two ml of synthetic fluid is insulted on the cover/absorbent system and the time for its absorption is recorded. The fluid is allowed to interact for 9 minutes in the system. A second two ml insult is applied and the time to absorb the fluid is recorded. The system is allowed again to interact for 9 minutes and the last two ml insult is then applied. The intake time is then recorded.

After the test, the length and width of the cover stain is measured and recorded. The stain areas were calculated by multiplying the stain length by the stain width.

While the invention has been described in detail with respect to specific aspects thereof, it will be appreciated that those skilled in the art, upon attaining an understanding of the foregoing, may readily conceive of alterations to, variations of and equivalents to these aspects. Accordingly, the scope of the present invention should be assessed as that of the appended claims and any equivalents thereto.

We claim:

1. A cover material comprising:
   a base material layer including a plurality of fine denier fibers, having a fiber denier of less than about 10 dpf; and
   a plurality of large denier filaments bonded to the base material layer, having a filament denier greater than about 10 dpf and forming a plurality of channels in the cover material.

2. The cover material of claim 1 wherein the fine denier fibers have a fiber denier of about 2 dpf to about 8 dpf.

3. The cover material of claim 1 wherein the fine denier fibers have a fiber denier of about 3 dpf to about 5 dpf.

4. The cover material of claim 1 wherein the cover material is treated with a surfactant.

5. The cover material of claim 4 wherein the surfactant is applied to a medial section along a longitudinal centerline of the cover material.

6. The cover material of claim 4 wherein the surfactant comprises a skin wellness treatment.

7. The cover material of claim 1 wherein the large denier filaments have a filament denier of about 10 dpf to about 100 dpf.

8. The cover material of claim 1 wherein the large denier filaments have a filament denier of about 15 dpf to about 40 dpf.

9. The cover material of claim 1 wherein the large denier filaments are colored.

10. The cover material of claim 1 wherein the large denier filaments each comprise a pigment.

11. The cover material of claim 1 wherein the large denier filaments are spaced between about 1 mm and about 15 mm.

12. The cover material of claim 1 wherein the large denier filaments are spaced between about 3 mm to about 8 mm.

13. The cover material of claim 1 wherein the base material layer comprises a spunbond web.

14. The cover material of claim 13 wherein the spunbond web is apertured.

15. The cover material of claim 1 wherein the fine denier fibers and the large denier filaments are bonded together by one of through-air bonding, ultrasonic bonding, adhesive bonding and combinations thereof.

16. The cover material of claim 1 wherein the channels are formed in a longitudinal direction of the cover material.

17. The cover material of claim 1 wherein the fine denier fibers and the large denier filaments comprise a polypropylene polymer.

18. The cover material of claim 1 wherein the fine denier fibers and the large denier filaments each comprises a polymer selected from the group consisting of polypropylene, polyethylene (high and low density), ethylene copolymers with $C_3$–$C_{20}$ α-olefins, propylene copolymers with ethylene or $C_4$–$C_{20}$ α-olefins, butene copolymers with ethylene, propylene, or $C_5$–$C_{20}$ α-olefins, polyvinyl chloride, polyesters, polyamides, polyfluorocarbons, polyurethane, polystyrene, polyvinyl alcohol, caprolactams, and cellulosic and acrylic resins.

19. The cover material of claim 18 wherein the fine denier fibers and the large denier filaments comprise the same polymer.

20. The cover material of claim 1 wherein the large denier filaments comprise an elastomeric material or an extensible material.

21. The cover material of claim 1 wherein the fine denier fibers comprise bicomponent fibers.

22. The cover material of claim 1 wherein the large denier filaments comprise bicomponent filaments.

23. A personal care product comprising the cover material of claim 1.

24. A diaper comprising the cover material of claim 1.

25. An adult incontinence product comprising the cover material of claim 1.

26. A feminine hygiene product comprising the cover material of claim 1.

27. A cover material comprising:
    a first nonwoven layer comprising a plurality of fine denier fibers, the fine denier fibers having a denier less than about 10 dpf; and
    a plurality of large denier filaments forming a plurality of channels, the large denier filaments having a denier greater than about 10 dpf.

28. The cover material of claim 27 wherein the large denier filaments have a filament denier of about 10 dpf to about 100 dpf.

29. The cover material of claim 27 wherein the large denier filaments have a filament denier of about 15 dpf to about 40 dpf.

30. The cover material of claim 27 wherein the fine denier fibers have a fiber denier of about 2 dpf to about 8 dpf.

31. The cover material of claim 27 wherein the fine denier fibers have a fiber denier of about 3 dpf to about 5 dpf.

32. The cover material of claim 27 wherein the fine denier fibers are thermally bonded to the large denier filaments.

33. The cover material of claim 27 wherein the cover material is treated with a surfactant.

34. The cover material of claim 33 wherein the cover material is selectively treated with the surfactant.

35. The cover material of claim 33 wherein the surfactant comprises a skin wellness treatment.

36. The cover material of claim 27 further comprising a second nonwoven layer.

37. The cover material of claim 36 wherein the second nonwoven layer has a wettability different than a wettability of the first nonwoven material.

38. The cover material of claim 36 wherein the second nonwoven layer has a permeability different than a permeability of the first nonwoven material.

39. The cover material of claim 36 wherein the second nonwoven layer has a pore size different than a pore size of the first nonwoven material.

40. The cover material of claim 36 wherein the second nonwoven layer has a void volume different than a void volume of the first nonwoven material.

41. The cover material of claim 36 wherein the cover material is apertured.

42. The cover material of claim 36 wherein the first nonwoven layer and the second nonwoven layer is coapertured.

43. The cover material of claim 27 wherein the plurality of large denier filaments form a plurality of streams disposed in a longitudinal direction of the first nonwoven layer.

44. The cover material of claim 27 wherein the large denier filaments are intermixed with the fine denier fibers.

45. A method for producing a multi-denier nonwoven material comprising the steps of:
    producing a base material layer comprising a plurality of fine denier fibers of less than about 10 dpf;
    combining a plurality of large denier filaments with the fine denier fibers to form a plurality of channels, the large denier filaments of at least about 10 dpf; and
    bonding the large denier filaments to the fine denier fibers.

46. The method of claim 45 wherein the fine denier fibers and the large denier fibers are bonded together by one of thermal bonding, through-air bonding, ultrasonic bonding, adhesive bonding and combinations thereof.

47. The method of claim 45 wherein the fine denier fibers and the large denier filaments comprise spunbond fibers.

48. The method of claim 45 wherein the fine denier fibers and the large denier filaments are spun from a spinning plate.

49. The method of claim 45 wherein the fine denier fibers are spun from a first spinning plate and the large denier filaments are spun from a second spinning plate.

50. The method of claim 45 wherein the fine denier fibers and the large denier filaments comprise a polypropylene polymer.

51. The method of claim 45 wherein the fine denier fibers and the large denier filaments each comprises a polymer selected from the group consisting of polypropylene, polyethylene (high and low density), ethylene copolymers with $C_3$–$C_{20}$ α-olefins, propylene copolymers with ethylene or $C_4$–$C_{20}$ α-olefins, butene copolymers with ethylene, propylene, or $C_5$–$C_{20}$ α-olefins, polyvinyl chloride, polyesters, polyamides, polyfluorocarbons, polyurethane, polystyrene, polyvinyl alcohol, caprolactams, and cellulosic and acrylic resins.

52. The method of claim 45 wherein the large denier filaments are added to the nonwoven material in an of-line process.

53. The cover material of claim 45 wherein the large denier filaments are intermixed with the fine denier fibers.

* * * * *